United States Patent [19]

Nöller

[11] 4,187,075

[45] Feb. 5, 1980

[54] METHOD OF ANALYZING BIOLOGICAL, LIQUID SPECIMENS FOR ANTIGENS OR ANTIBODIES

[76] Inventor: Hans G. Nöller, 1512 Basswood Cir., Glenview, Ill. 60025

[21] Appl. No.: 769,044

[22] Filed: Feb. 16, 1977

Related U.S. Application Data

[63] Continuation-in-part of Ser. No. 689,335, May 24, 1976.

[30] Foreign Application Priority Data

May 26, 1975 [DE] Fed. Rep. of Germany ....... 2523209
Feb. 21, 1976 [DE] Fed. Rep. of Germany ....... 2607149

[51] Int. Cl.$^2$ ................... G01N 33/16; G01N 21/38; G01N 31/14
[52] U.S. Cl. .................. 23/230 B; 23/230.6; 424/1; 424/8; 424/12; 435/7
[58] Field of Search ............... 23/230 B, 230.6; 424/8, 424/12, 1, 1.5; 195/103.5 A

[56] References Cited

U.S. PATENT DOCUMENTS

| | | | |
|---|---|---|---|
| 3,646,346 | 2/1972 | Catt | 23/230 B X |
| 3,790,663 | 2/1974 | Garrison | 424/12 |
| 3,826,619 | 7/1974 | Bratu | 23/230 B X |
| 3,843,324 | 10/1974 | Edelman | 23/230 B |
| 4,016,043 | 4/1977 | Schuurs | 195/103.5 R |
| 4,020,151 | 4/1977 | Bolz | 424/1.5 |

*Primary Examiner*—Sidney Marantz
*Attorney, Agent, or Firm*—Toren, McGeady and Stanger

[57] ABSTRACT

A human body fluid is analyzed for the presence of one member of the group consisting of an antigen and an antibody capable of specifically combining with the antigen by depositing a specimen of the fluid to be analyzed on an inert solid substrate and by volatilizing the water in the specimen under mild conditions which leave the one member as a deposit on the surface of the substrate. The surface then is contacted with the other member, which carries a labeling agent, for a period sufficient for combining the members if the one member is present. Any amount of the labeled member not combined with the one member thereafter is removed, and a sensible signal indicative of the presence of labeing agent on the substrate is generated.

11 Claims, No Drawings

METHOD OF ANALYZING BIOLOGICAL, LIQUID SPECIMENS FOR ANTIGENS OR ANTIBODIES

This application is a continuation-in-part of my copending application, Ser. No. 689,335, filed May 24, 1976.

This invention relates to the detection and determination of antigens and antibodies in clinical specimens of blood and other body fluids, and more particularly to a method of analyzing liquid specimens for dispersed antigens and antibodies.

In the afore-mentioned earlier application, I disclosed and claimed a method and apparatus for determining antigens and antibodies by a fluoroimmunoassay simpler than the radio-immunoassay methods now in common clinical use. I have now found that antigens and antibodies can be detected and determined quantitatively in an even simpler manner by a method utilizing some aspects of the earlier invention, but not necessarily limited to the analysis for fluorescent labeling agents.

It is a primary object of this invention to provide a method which permits antigens or antibodies to be detected and determined quantitatively in a very short time.

According to this invention, as applied to the detection or determination of antibodies, a specimen of the liquid to be analyzed is deposited on an inert solid substrate. The liquid in the specimen is volatilized under conditions which leave the antibodies present, if any, as an unaltered deposit on the surface of the substrate. The surface then is contacted with antigens capable of specifically combining with the antibodies and carrying a labeling agent for a period sufficient for combining the antigens and antibodies in an immune reaction if antibodies are present. Any uncombined antigens are then removed from the substrate surface, and a sensible signal indicative of the presence of residual labeling agent on the substrate is generated. Antigens and antibodies are interchangeable in this procedure so that the method may equally be employed for detecting and determining antigens in a specimen.

While the invention will be described hereinafter with reference to its presently most important, practical application, the analysis of human blood for use in a blood bank, it is generally applicable to body fluids not necessarily of human origin, including urine, cerebrospinal liquor, saliva, liquid dispersions of feces, and the like, and may be used for determining isolated antigens and antibodies dispersed in a liquid not originating from a living body.

The nature of the substrate on which the specimen is deposited is unimportant as long as the substrate is inert to the specimen and to other materials with which it comes into contact during the analysis. Glass, many plastics and metals are among the materials which meet this requirement. It is advantageous to employ a substrate which favors spreading of the deposited specimen in a thin film, but this is not critical.

Because of the very small amounts of specimen needed in this invention, the liquid in the specimen, normally water, is volatilized spontaneously at ambient temperature within a minute so that the biological material in the specimen is not altered in any way. To avoid or minimize loss of the residue obtained after volatilizing the water, the proteinaceous material left on the substrate surface is preferably fixed to the substrate surface. Denaturing by means of an organic solvent miscible with water is most convenient, but other fixatives conventional in themselves may be resorted to, such as osmium oxide.

The amount of labeled material brought into contact with the residue is chosen to suit the desired result. If it is intended merely to establish the presence or absence of a minimum amount of antigen or antibody, the amount of labeled antibody or antigen may be smaller than that capable of being combined with the residual biological material. If a quantitative analysis of the specimen is required, an excess of labeled material is normally necessary, and the excess is removed prior to analysis for the labeling agent in the combined material.

The nature of the labeling agent is not critical in itself. Known labeling agents employed in immunoassays include radio-isotopes, but also such non-isotopic labels as enzymes, erythrocytes, bacteriophages, fluorescent dyes, and stable radicals. A recent, comprehensive bibliography of labeling methods, particularly for enzyme-immunoassay, by G. Brain Wisdom is found in Clinical Chemistry 22 (8) 1243-1255 (1976). Convenient methods of generating a sensible signal indicative of the presence or of the amount of the labeling agent on the substrate of this invention after removal of uncombined labeled material are available at this time for labeling radioactive isotopes, enzymes, and fluorescent dyes, and will be described in more detail hereinafter.

An important advantage of this invention is the relatively short contact time necessary for combining antigens and antibodies, and the fact that reproducible results can be achieved without precisely controlling the contact time. One hour is amply adequate for quantitative analysis under practically all conditions, longer periods are not harmful, and shorter periods may be chosen where only a qualitative indication is needed.

The nature of the sensible signal generated is not directly relevant to this invention. It will usually be visible, but an audible signal may be preferred under suitable conditions. The primary signal may be electrical and may be converted to the desired sensible signal, but it will be shown hereinbelow that a sensible signal may be produced directly by the labeling agent bound to the biological material of the specimen on the substrate.

The following Examples are illustrative of the method of this invention.

EXAMPLE 1

A droplet of human blood plasma (100 µl) was placed on a piece of nylon net (200 mesh), one inch square, and permitted to dry. The fabric carrying the dried residue was immersed in acetone for five minutes to fix the plasma solids, and the solvent was permitted to evaporate at ambient temperature. The net then was rolled up to fit into a test tube 50 mm long and 6 mm in diameter, 0.5 ml 125 I-tagged human hepatitis associated antibody solution (a commercial product of Abbott Laboratories) was added to cover the dried material on the net, and the tube was placed in a laboratory oven at 20° C. for 60 minutes.

The net then was washed three times for 30 seconds in 40 ml saline and airdried. Its radioactivity was determined with a scintillation counter, and 1500 counts per minute were obtained. For comparison purposes, the procedure was repeated with several blood plasma specimens known to be free from hepatitis associated antigen, and fewer than 400 counts per minute were obtained.

In a series of tests on blood specimens containing hepatitis-associated antigen, all readings were between 800 and 16,000 counts per minute and were closely related to conventionally obtained control analyses.

EXAMPLE 2

A droplet of plasma was permitted to dry on a one inch square of nylon net and was fixed in acetone as in Example 1. The net was rolled as needed to insert it into a 50×6 mm test tube. 500 μl hepatitis B antibodies, flurescein conjugated, in aqueous dispersion, a commercial product available from Behringwerke AG, Germany, was diluted with 10 volumes buffer solution (pH 7.1) and added to the nylon net in the tube which was thereafter held at 20° C. for 60 minutes.

The nylon net was washed twice in 40 ml of a 2:1 (vol.) mixture of saline and acetone, and once in acetone, each washing taken about 30 seconds. After airdrying, the net was soaked 10 minutes in 3 ml one-normal sodium hydroxide solution and thereafter discarded. The alkaline solution was exposed to a single light flash of $10^{-4}$ second in the apparatus described in the aforementioned application, and the resulting fluorescene was indicated as the output voltage of a photomultiplier tube circuit. The measured voltage of less than 1.5 volts indicated the absence of hepatitis antigen in the plasma specimen.

A series of approximately 1500 tests following the same procedure gave readings between 1.5 and 15 volts on specimens in which hepatitis antigens could also be detected by conventional radioimmuno assay.

EXAMPLE 3

A plasma specimen was applied to a square of nylon net, dried and fixed as in the preceding examples, and inserted into a test tube. It was incubated for 60 minutes at 37° C. with 0.5 ml horseradish peroxidase conjugated hepatitis B antibodies and thereafter washed three times with 40 ml buffer solution (pH 7.1) containing 0.9% NaCl.

The nylon net then was immersed 15 minutes in 10 ml of a solution prepared from 50 mM Tris buffer (pH 7.4) containing 5 mg 3,3'-diaminobenzidine and 0.036% hydrogen peroxide, whereby a blue spot was developed on the net. The spot was eluted by shaking the net with 3 ml of a 2:1 (vol.) mixture of saline and acetone, and the resulting blue solution was analyzed in a spectrophotometer.

A series of tests performed in this manner on serum specimens containing known amounts of hepatitis antigen yielded an empirical chart of photometer readings as a function of antigen concentration. Specimens free from antigen yielded eluates of a very faint blue color, but the intensity of the color increased rapidly with increasing amounts of antigen bound to the net.

It should be understood, of course, that the foregoing disclosure relates only to presently preferred embodiments of the invention, and that it is intended to cover all changes and modification of the invention herein chosen for the purpose of the disclosure which do not constitute departures from the spirit and scope of the invention set forth in the appended claims.

What is claimed is:

1. A method of analyzing a volatile liquid for the presence therein of one member of the group consisting of an antigen and an antibody capable of specifically combining with said antigen, said one member being dispersed in said liquid, and the other member of said group carrying a labeling agent which method comprises:
   (a) depositing a specimen of said liquid on an inert solid substrate;
   (b) volatilizing said liquid under conditions leaving said one member as a deposit on the surface of said substrate;
   (c) holding said deposit in contact with a fixing agent for a period sufficient to fix said one member to said substrate;
   (d) contacting said surface with said other member for a period sufficient for combining said members if said one member is present;
   (e) removing from said surface any amount of said other member not combined with said one member; and
   (f) generating a sensible signal indicative of the presence of said labeling agent on said substrate after said removing.

2. A method as set forth in claim 1, wherein said substrate is a fabric of synthetic fibers.

3. A method as set forth in claim 2, wherein said fibers essentially consist of nylon.

4. A method as set forth in claim 1, wherein said fixing agent is an organic solvent miscible with water.

5. A method as set forth in claim 4, wherein said organic solvent is capable of denaturing said deposit.

6. A method as set forth in claim 1, wherein the amount of liquid matter in said specimen is small enough to permit volatilizing thereof in not substantially more than one minute in contact with ambient air at ambient temperature.

7. A method as set forth in claim 6, wherein said period is not substantially greater than one hour.

8. A method as set forth in claim 6, wherein said liquid is aqueous.

9. A method as set forth in claim 8, wherein said labeling agent is a radioactive isotope, a fluorescent material, or an enzyme.

10. A method as set forth in claim 6, wherein said one member is an antigen.

11. A method as set forth in claim 10, wherein said one member is hepatitis-associated antigen, said liquid being an aqueous solution of human plasma.

* * * * *